United States Patent [19]

Doherty et al.

[11] 4,374,997

[45] Feb. 22, 1983

[54] PROCESS FOR THE PREPARATION OF ZOMEPIRAC AND RELATED COMPOUNDS

[75] Inventors: James B. Doherty, New Milford; Debra L. Allison, Scotch Plains, both of N.J.

[73] Assignees: Merck & Co., Inc, Rahway, N.J.

[21] Appl. No.: 270,317

[22] Filed: Jun. 4, 1981

[51] Int. Cl.$^3$ ................. C07D 207/337; C07D 207/31
[52] U.S. Cl. ...................................................... 548/539
[58] Field of Search ..................................... 260/326.47

[56] References Cited

U.S. PATENT DOCUMENTS

| | | | |
|---|---|---|---|
| 3,752,826 | 8/1973 | Carson | 260/326.47 |
| 3,952,012 | 4/1976 | Carson | 260/326.47 |
| 4,048,191 | 9/1977 | Carson | 260/326.47 |
| 4,070,368 | 1/1978 | Carson | 260/326.47 |

OTHER PUBLICATIONS

Finai; Org. Chem., 2, 5th ed., p. 670, (1975).
Carson et al.; J. Med. Chem., vol. 16, No. 2, p. 173, (1973).
Patai, S. (editor); *Chem. Carboxylic Acids and Esters*, Chap. 12, p. 589, (1969).

*Primary Examiner*—Mary C. Lee
*Attorney, Agent, or Firm*—Theresa Y. Cheng; Mario A. Monaco

[57] ABSTRACT

Zomepirac and its analogs have been prepared from a 5-aroyl-3-hydroxycarbonyl-4-substituted pyrrole-2-acetic acid via acidic decarboxylation.

9 Claims, No Drawings

PROCESS FOR THE PREPARATION OF ZOMEPIRAC AND RELATED COMPOUNDS

BACKGROUND OF THE INVENTION

This invention relates to an improved process involving decarboxylation. Specifically, it involves the preparation of Zomepirac and analogs via acidic decarboxylation.

Decarboxylation via heterolytic cleavages generally fall into two catalogues:

I. Decarboxylation of acids whose anions are less stable with respect to decarboxylation than the unionized acid; and II. Decarboxylation of acids whose unionized form is more susceptible to decarboxylation than their anions.

For most acids, decarboxylation (Catalogue I) takes place in a basic medium, i.e., in their anion forms. However, for $\alpha$ or $\beta$-keto acids, decarboxylation (Catalogue II) usually undergoes much easier in an acidic medium, i.e., in their unionized free acid forms. The keto acids' exceptional preference for acidic decarboxylation is attributed to the following mechanism:

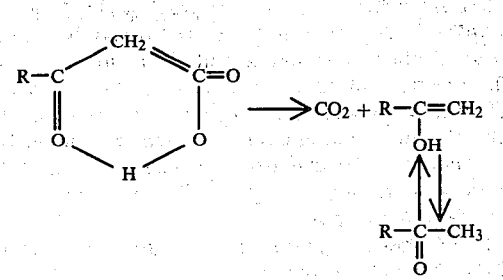

Zomepirac and its analogs are useful anti-inflammatory agents of the structural formula (I).

These compounds have been previously prepared in four steps by decarboxylation of a diester, (II).

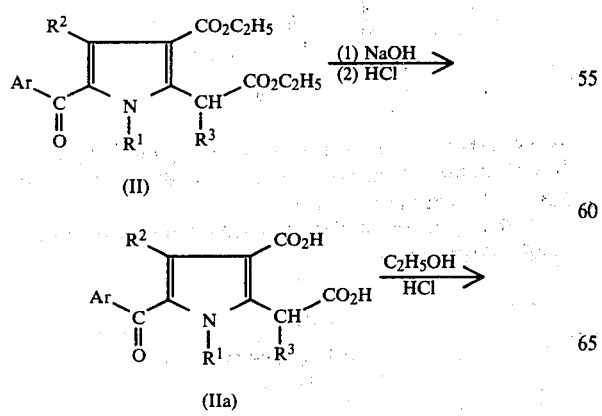

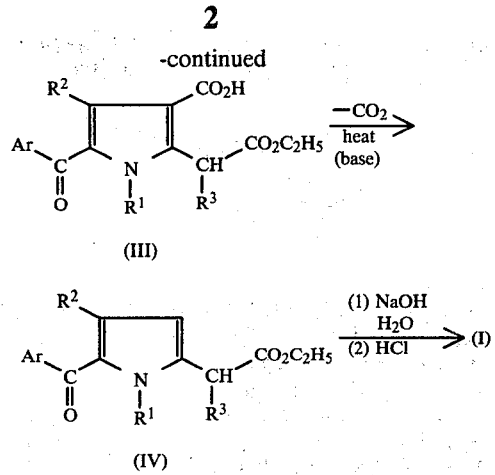

It has been known that heterocyclic acids of similar structural features, for example, pyridine-3-carboxylic acid and thiazole-4-carboxylic acid, decarboxylate more rapidly in basic media than in acid solvents (Patai, The Chemistry of Carboxylic Acids and Esters, Interscience, N.Y., 1969, pg. 602).

The prior art decarboxylation as described above is usually conducted in an organic base such as quinoline or neat at relatively high temperatures. To preserve selectivity of decarboxylation, protection of the acetic acid is required under the drastic conditions. Accordingly, two extra steps, i.e., (a) the preparation of the monoester (III); and
(b) the hydrolysis of ester (IV) to afford (I) are added to the process making it a 4-step process.

As expected, the overall yields of the prior art process are generally lower due to the additional steps and the more drastic conditions of the decarboxylation.

To the contrary, the present process relates to a single-step acidic decarboxylation by which pyrrole acetic acids of formula (I) are unexpectedly prepared from diacid (IIa) under mild conditions:

As shown above, the tedious blocking and deblocking steps are eliminated, and the drastic decarboxylation condition is avoided. Both contribute to the excellent yield of compound (I) (90–95%).

DETAILED DESCRIPTION OF THE INVENTION

The present invention is concerned with a single-step process for preparing Zomepirac and its analogs of the structural formula (I):

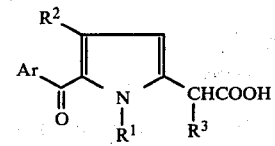

wherein Ar is phenyl or halophenyl such as 4-chloro, 4-fluoro, 3-chloro or 2-fluorophenyl preferably 4-chlorophenyl; $R^1$ and $R^3$ independently are H, or lower alkyl especially $C_{1-6}$ alkyl such as methyl, ethyl, n-propyl, butyl, pentyl or hexyl; and $R^2$ is H, lower alkyl especially $C_{1-6}$ alkyl as previously defined, or halo such as fluoro or chloro, comprising acidic decarboxylation of a compound of the structural formula (II):

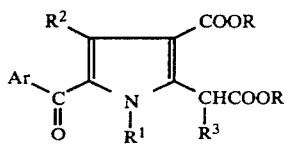 (II)

wherein $R^1$, $R^2$ and $R^3$ are as previously defined; and R is H, t-butyl, benzhydryl or other protecting groups which are easily removed in trifluoroacetic acid or other related organic acids.

The acidic decarboxylation is conducted under mild conditions. For example, 5-(p-chlorobenzoyl)-3-hydroxycarbonyl-4-methylpyrrole-2-acetic acid is treated with refluxing trifluoroacetic acid to afford 5-(p-chlorobenzoyl)-4-methylpyrrole-2-acetic acid. Other acids may also be used. For example, those listed below in Table I.

TABLE I

Acids Used in the Decarboxylation (1) An acid of the structural formula:

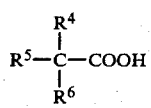

wherein $R^4$ and $R^6$ independently are hydrogen or halo such as iodo, bromo, chloro or fluoro preferably chloro or fluoro; and $R^5$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.

(2) Preferred Acids:
Acetic acid
Chloroacetic acid
Chlorodifluoroacetic acid
Dichloroacetic acid
Difluoroacetic acid
Trichloroacetic acid
Pentafluoropropanoic acid
Trifluoroacetic acid The decarboxylation may be conducted in an acid or in a inert solvent containing the acid. The solvents which are often used are illustrated below in Table II.

TABLE II

Solvents for the Acidic Decarboxylation

Toluene
Benzene
Xylene
Tetrahydrofuran
1,2-Dimethoxy-ethane
Dioxane

The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 72° C.

Generally, the decarboxylation is substantially complete after heating at an appropriate temperature for about 1 to about 20 hours or under more favorable conditions, about 0.5 hours to about 5 hours.

The starting pyrrole diacids of the present process are prepared readily from the procedures disclosed in U.S. Pat. No. 3,752,826 and is incorporated herein by reference.

EXAMPLE 1

Decarboxylation of 5-(p-chlorobenzoyl)-1,4-dimethyl-3-hydroxycarbonyl-pyrrole-2-acetic acid Two hundred and thirty-five milligrams of 5-(p-chlorobenzoyl)-1,4-dimethyl-3-hydroxycarbonyl-pyrrole-2-acetic acid is dissolved in 5 ml of trifluoroacetic acid and the resulting solution is heated to reflux for 1.5 hours. After most of the solvent is removed *in vacuo*, the residue is treated with 10 ml of water. The resulting residue is filtered and dried *in vacuo* to give 5-(p-chlorobenzoyl)-1,4-dimethyl-pyrrole-2-acetic acid (Zomepirac) in 91% yield, m.p. 184°–185° C.

EXAMPLE 2

Decarboxylation of 5-(p-fluorobenzoyl)-3-hydroxycarbonyl-1,4-dimethyl-pyrrole-2-acetic acid 5-(p-fluorobenzoyl)-3-hydroxycarbonyl-1,4-dimethylpyrrole-2-acetic acid (1 mmole) is dissolved in 5 ml tetrahydrofuran containing 2 ml of trichloroacetic acid. The reaction mixture is heated to reflux for 5 hours before it is evaporated *in vacuo* to remove most of the solvent. The resulting oil is triturated with about 10 ml of water, filtered and dried *in vacuo* to afford 5-(p-fluorobenzoyl)-4-methylpyrrole-2-acetic acid.

What is claimed is:

1. A process for preparing Zomepirac and its analogs of the structural formula:

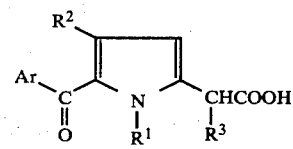 (I)

wherein Ar is phenyl or halophenyl; $R^1$ and $R^3$ independently are H or $C_{1-6}$alkyl and $R^2$ is H, $C_{1-6}$alkyl or halo comprising decarboxylating a diacid derivative of the structural formula:

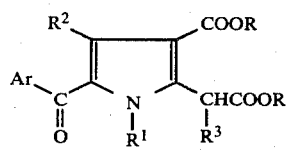 (II)

wherein $R^1$, $R^2$ and $R^3$ are as previously defined; and R is H, t-butyl, or benzhydryl in an acid or in an inert solvent containing the acid.

2. The process of claim 1 wherein the acid is of the structural formula:

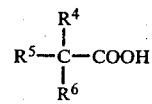

wherein $R^4$ and $R^6$ independently are hydrogen or halo; $R^5$ is H, $C_{1-6}$alkyl, halo or halo-$C_{1-6}$alkyl.

3. The process of claim 2 wherein $R^4$ and $R^6$ independently are chloro or fluoro; and $R^5$ is H, chloro, fluoro, or halo-$C_{1-6}$ alkyl.

4. The process of claim 2 wherein the acid is:
Acetic acid;
Chloroacetic acid;
Chlorodifluoroacetic acid;
Dichloroacetic acid;
Difluoroacetic acid;
Trichloroacetic acid;
Pentafluoropropanoic acid; or
Trifluoroacetic acid.

5. The process of claim 2 wherein the acid is trifluoroacetic acid.

6. The process of claim 4 wherein the solvent is:
Toluene;
Benzene;
Xylene;
Tetrahydrofuran;
1,2-Dimethoxyethane; or
Dioxane.

7. The process of claim 1 wherein the solvent is toluene, benzene, xylene, tetrahydrofuran, 1,2-dimethoxyethane or dioxane and the acid is acetic acid, chloroacetic acid, chlorodifluoroacetic acid, dichloroacetic acid, difluoroacetic acid, trichloroacetic acid, pentafluoropropanoic acid or trifluoroacetic acid.

8. The process of claim 1 for preparing Zomepirac wherein the diacid derivative is 5-(p-chlorobenzoyl)-3-hydroxycarbonyl-1,4-dimethylpyrrole-2-acetic acid; and the acid is trifluoroacetic acid.

9. The process of claim 1 wherein the diacid derivative is t-butyl 5-(p-chlorobenzoyl)-3-butoxycarbonyl-1,4-dimethylpyrrole-2-acetate.

* * * * *